United States Patent
Winston et al.

(10) Patent No.: US 6,230,568 B1
(45) Date of Patent: *May 15, 2001

(54) METHOD AND APPARATUS FOR ULTRASONIC INSPECTION OF INACCESSIBLE AREAS

(75) Inventors: Thomas R. Winston, Leawood; John A. Brunk, Overland Park, both of KS (US)

(73) Assignee: Ultrasonic Sensing and Monitoring Systems, Inc., Leawood, KS (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/582,231

(22) Filed: Jan. 3, 1996

Related U.S. Application Data

(63) Continuation of application No. 08/386,330, filed on Feb. 10, 1995, now abandoned, which is a continuation of application No. 08/193,612, filed on Feb. 8, 1994, now abandoned, which is a continuation of application No. 07/832,816, filed on Feb. 7, 1992, now abandoned.

(51) Int. Cl.$^7$ ..................................................... G01N 29/06
(52) U.S. Cl. ................................ 73/601; 73/644; 73/592; 606/15
(58) Field of Search ........................... 73/644, 601, 592, 73/622, 40.5 A; 376/245, 248, 252, 249; 385/116, 117, 118; 128/662.06; 606/15

(56) References Cited

U.S. PATENT DOCUMENTS

| | | |
|---|---|---|
| 3,264,863 * | 8/1966 | Maropis ................................ 376/245 |
| 3,470,868 | 10/1969 | Krause et al. . |
| 3,779,234 | 12/1973 | Eggleton et al. . |
| 3,915,018 * | 10/1975 | Karplus ................................ 376/245 |
| 3,938,502 | 2/1976 | Bom . |

(List continued on next page.)

FOREIGN PATENT DOCUMENTS

| | | |
|---|---|---|
| 0325836 | 8/1989 | (EP) . |
| 0329492 | 8/1989 | (EP) . |
| 0127665 * | 6/1987 | (JP) ........................................ 73/631 |
| 62-270140 | 11/1987 | (JP) . |
| 376712 * | 4/1973 | (SU) ....................................... 73/644 |
| 8701269 * | 3/1987 | (WO) . |
| WO 8701269 | 3/1987 | (WO) . |

OTHER PUBLICATIONS

Zeiss Publication and Translation.
"Similarities and Differences Between Fiber Acoustics and Fiber Optics" C.K. Jen, Dated 1985.

Primary Examiner—Hezron Williams
Assistant Examiner—Nashmiya Fayyaz
(74) Attorney, Agent, or Firm—Armstrong Teasdale LLP

(57) ABSTRACT

A method and apparatus which uses ultrasonic techniques to inspect critical pipe joints and other critical industrial areas that are normally inaccessible. A waveguide including one or more flexible fibers is embedded in concrete or whatever else embeds the piping which includes the critical area. One end of the waveguide is accessible so that an ultrasonic transducer can be used to transmit ultrasonic signals along the waveguide and receive reflected echoes to provide an ultrasonic image of the critical area. In a case where the area to be inspected is submerged, the waveguide takes the form of a flexible fiber bundle which is manipulated until its end is adjacent to the critical area. Some of the fibers in the bundle can be used to illuminate the critical area, and other fibers can transmit optical images for display on a video monitor. In an alternative embodiment, a single optical fiber waveguide is used to transmit illumination, optical signals and ultrasonic signals.

9 Claims, 2 Drawing Sheets

U.S. PATENT DOCUMENTS

| | | | |
|---|---|---|---|
| 4,008,455 | * | 2/1977 | Pedersen ................ 376/245 |
| 4,208,917 | * | 6/1980 | Aoyama et al. ............ 73/644 |
| 4,284,473 | * | 8/1981 | Kasama ................... 376/245 |
| 4,337,661 | | 7/1982 | Kretz ..................... 73/628 |
| 4,349,032 | | 9/1982 | Koyata .................... 73/644 |
| 4,462,408 | * | 7/1984 | Silverstein et al. ........ 128/662.06 |
| 4,466,443 | | 8/1984 | Utsugi . |
| 4,576,177 | | 3/1986 | Webster, Jr. . |
| 4,587,972 | | 5/1986 | Morantte . |
| 4,605,009 | * | 8/1986 | Pourcelot et al. .......... 128/662.06 |
| 4,757,818 | | 7/1988 | Angelsen ................... 73/633 |
| 4,764,334 | * | 8/1988 | King et al. ............... 376/248 |
| 4,794,931 | | 1/1989 | Yock ...................... 128/660.03 |
| 4,869,258 | | 9/1989 | Hetz ...................... 128/660.1 |
| 4,887,605 | | 12/1989 | Angelsen et al. ........... 128/660.03 |
| 4,930,515 | | 6/1990 | Terwilliger ............... 128/662.06 |
| 4,950,267 | | 8/1990 | Ishihara et al. . |
| 4,951,677 | | 8/1990 | Crowley et al. . |
| 4,957,112 | | 9/1990 | Yokoi et al. .............. 128/662.06 |
| 4,972,839 | | 11/1990 | Angelsen .................. 128/662.06 |
| 5,010,886 | | 4/1991 | Passafaro et al. .......... 128/660.03 |
| 5,022,399 | * | 6/1991 | Biegeleisen ............... 128/662.06 |
| 5,024,092 | * | 6/1991 | Harrold et al. ............ 73/644 |
| 5,029,588 | | 7/1991 | Yock et al. ............... 128/662.06 |
| 5,054,492 | | 10/1991 | Scribner et al. ........... 128/662.06 |
| 5,152,291 | | 10/1992 | Dias ...................... 128/661.08 |
| 5,159,920 | * | 11/1992 | Condon et al. ............. 128/662.06 |
| 5,163,432 | | 11/1992 | Ueno et al. ............... 128/660.03 |
| 5,170,793 | | 12/1992 | Takano et al. ............. 128/662.06 |
| 5,195,519 | | 3/1993 | Angelsen .................. 128/662.06 |
| 5,217,018 | * | 6/1993 | Dias ...................... 128/662.06 |
| 5,254,112 | | 10/1993 | Sinofsky et al. ........... 606/7 |
| 5,257,628 | | 11/1993 | Ishiguro et al. . |
| 5,284,148 | * | 2/1994 | Dias et al. ............... 128/662.06 |
| 5,350,377 | * | 9/1994 | Winston et al. ............ 606/15 |
| 5,977,538 | * | 11/1999 | Unger et al. .............. 250/227.2 |

* cited by examiner

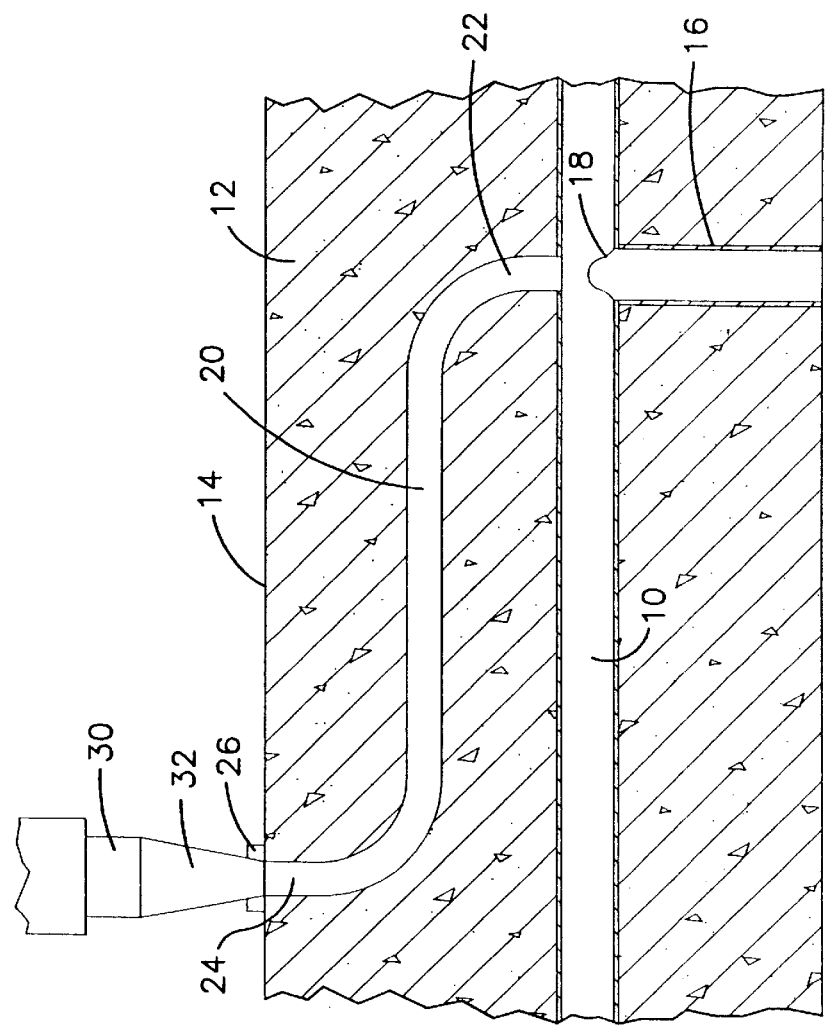
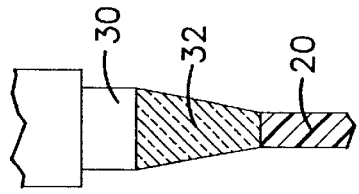
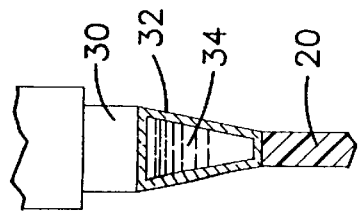
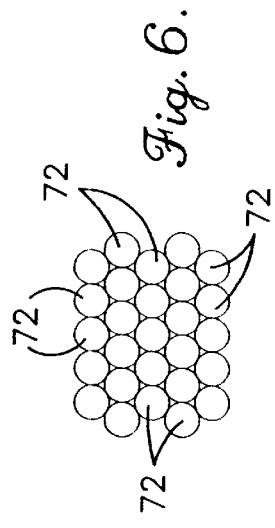
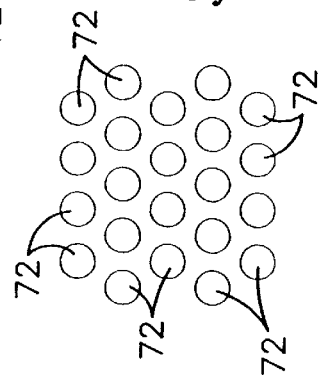

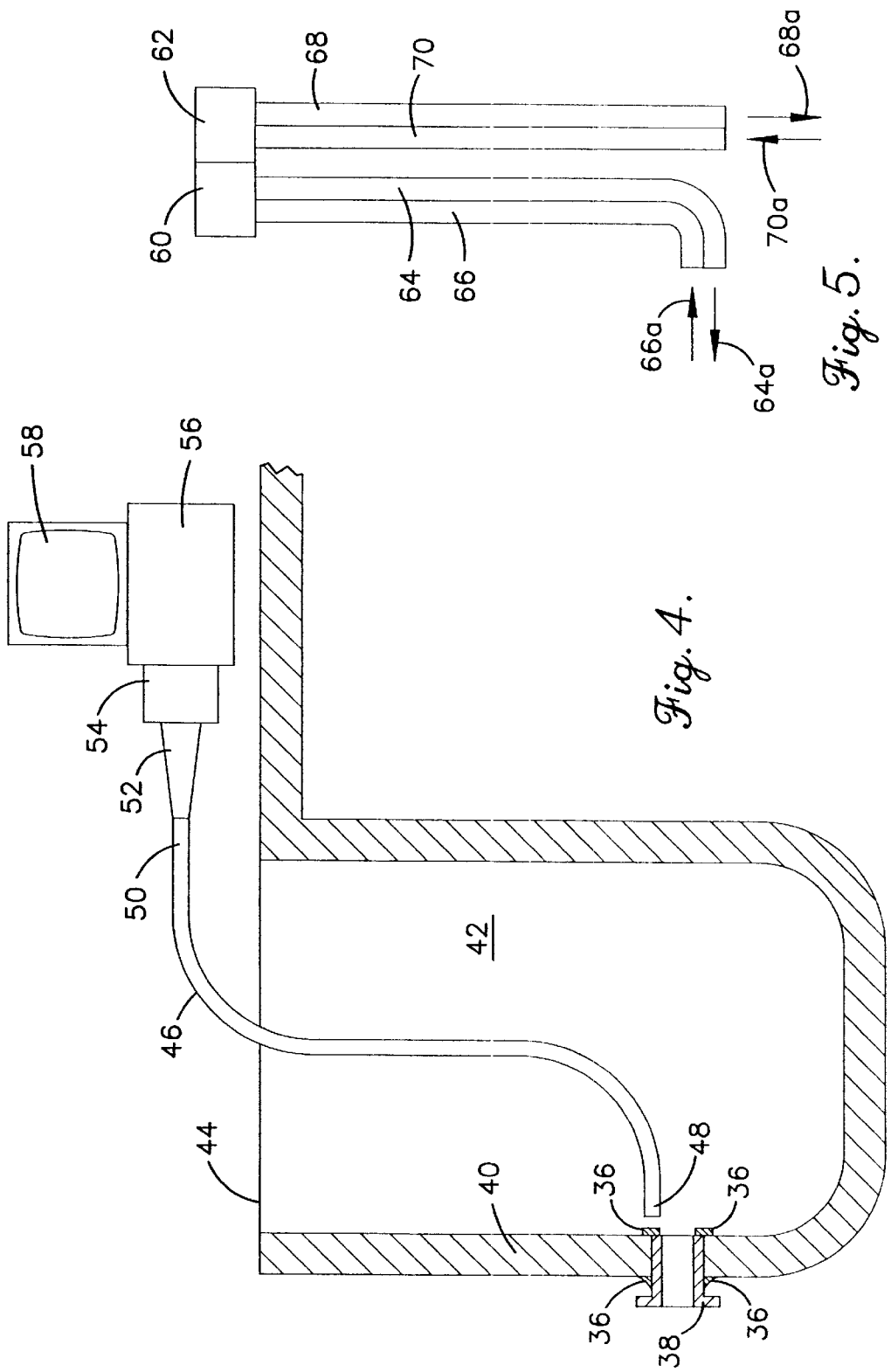

US 6,230,568 B1

METHOD AND APPARATUS FOR ULTRASONIC INSPECTION OF INACCESSIBLE AREAS

This application is a File Wrapper Continuation of Ser. No. 08/386,330, filed Feb. 10, 1995 now abandoned, which is a continuation of Ser. No. 08/193,612, filed Feb. 8, 1994 now abandoned, which is a continuation of application Ser. No. 07/832,816, filed Feb. 7, 1992 now abandoned.

FIELD OF THE INVENTION

This invention relates generally to ultrasonic imaging and deals more particularly with the use of ultrasonic techniques for the inspection of areas to which access is restricted.

BACKGROUND OF THE INVENTION

In a variety of industrial processes, there are areas that are inaccessible and yet at the same time critical to the process. For example, pipes which conduct the flow of process fluids are often embedded in concrete or a similar material such that inspection of critical pipe joints is impossible. If a faulty weld exists or if a critical area should otherwise fail while the pipes are in service, the lack of ability to carry out inspections creates a situation where no warning is given of a possibly dangerous condition. As an example, in a nuclear power plant or other critical facility, if piping which conducts cooling fluid should leak, disastrous consequences can follow. If the piping is capable of being inspected on a regular basis, the problem can be detected early enough to allow corrective action to be taken before there is a complete failure.

Similar situations arise as to pipes and fittings that are submerged in storage tanks for petroleum based liquids and other types of liquids. Access to submerged areas is restricted if not precluded altogether, so leaks and other problems can arise without any warning because inspections of the submerged areas are not practical and perhaps not even possible. The same problems are presented as to inspections in hostile environments such as areas exposed to the high levels of radiation or toxic chemicals.

SUMMARY OF THE INVENTION

The present invention is directed to a method and apparatus for carrying out ultrasonic inspections and examinations of locations that are normally inaccessible and thus not subject to inspection. By way of example, through the techniques employed by the present invention, a critical pipe weld which is embedded in a concrete slab can be inspected while the piping remains in service. Accordingly, signs of problems in the weld can be detected before they become so great that the weld fails. In addition, submerged components and structures located in hostile environments can be inspected to detect problems before they have developed to the point of complete failure.

In accordance with the invention, a waveguide for transmitting ultrasonic signals takes the form of at least one and usually a number of quartz fibers arranged in a bundle. In the case of a pipe weld or other critical part which is embedded in concrete or another material, the waveguide may also be embedded with one end adjacent to the weld that is to be inspected and the other end situated at the surface of the concrete or at another accessible location. A conventional ultrasonic transducer can be permanently or detachably connected to the accessible end of the waveguide and used to transmit ultrasonic signals and receive signals that are reflected back to the waveguide from the critical weld. In this manner, an ultrasonic image can be generated of the critical area and examined to give a warning of any problems that may exist.

In the case of a part that is submerged well below the surface of a liquid, the waveguide can be manipulated in the liquid using conventional techniques to position its end adjacent to the submerged part. Then, an ultrasonic transducer system above the liquid can be used to apply signals to the waveguide and receive reflected signals in order to provide an ultrasonic image of the part. The image that is generated can be examined for signs of damage or impending failure. The fibers can include some which transmit ultrasonic signals, others which are used for illumination of the tip end of the waveguide, and still others which transmit optical images. With the use of a video monitor, the operator of the apparatus can actually observe on the monitor how the waveguide tip is positioned relative to the part that is undergoing inspection. In many situations, this can enhance the accuracy of the procedure and the overall effectiveness of the inspection process.

It is an important feature of the invention that the ultrasonic waveguide is flexible. This allows it to be manipulated to provide access to areas that are at best difficult to reach with conventional rigid waveguides. The considerable length of the waveguide also provides it with the capability of making relatively remote areas accessible for inspection.

DESCRIPTION OF THE DRAWINGS

In the accompanying drawings which form a part of the specification and are to be read in conjunction therewith and in which like reference numerals are used to indicate like parts in the various views:

FIG. 1 is a fragmentary sectional view illustrating how the apparatus of the present invention can be used to monitor a critical pipe joint that is embedded in concrete;

FIG. 2 is a fragmentary sectional view showing one way of coupling a quartz fiber with an ultrasonic transducer in accordance with the invention;

FIG. 3 is a fragmentary sectional view similar to FIG. 2, but showing a different way of coupling a fiber to the ultrasonic transducer;

FIG. 4 is a diagrammatic view showing how the apparatus of the present invention can be used to inspect a component that is submerged in a tank containing liquid;

FIG. 5 is a diagrammatic view depicting the use of a dual element transducer and different waveguides oriented in different directions in accordance with the invention;

FIG. 6 is an end elevational view of quartz fibers which are arranged in a bundle having the fibers closely packed together; and FIG. 7 is an end view similar to FIG. 6, but showing the fibers in the bundle arranged in ordered rows.

DETAILED DESCRIPTION OF THE INVENTION

Referring now to the drawings in more detail and initially to FIG. 1, numeral 10 designates a horizontal pipe which is embedded in a concrete slab 12 having only its upper surface 14 accessible. A vertical pipe 16 is connected with the horizontal pipe 10 by a weld 18. The pipes 10 and 16 may carry industrial process fluids, and the weld 18 may be at a critical area in which weld failure could lead to the leakage of the process fluid or other adverse consequences. The piping system may be a critical one such as a system which conducts cooling fluid for a nuclear power plant or some other critical facility. Because the pipes 10 and 16 are embedded in the concrete 12, the weld 18 is not accessible for inspection. The concrete 12 is relatively impervious to ultrasonic signals so that ultrasonic signals applied from the accessible surface 14 cannot be used in a practical manner for reliable inspection of the weld 18.

In accordance with the present invention, a flexible waveguide 20 is embedded in the concrete slab 12 when it is poured or otherwise initially constructed. The waveguide 20 is arranged with its free end 22 located adjacent to and pointed at the weld 18. The waveguide 20 may have a serpentine shape or any other suitable shape, and its opposite end 24 is located adjacent to the accessible surface 14 or at some other accessible location. A collar 26 located on top of the slab surface 14 provides a port to permit detachable connection of ultrasonic equipment to the accessible end 24 of the waveguide 20 as will be explained in more detail.

A conventional ultrasonic pulser-receiver controls an ultrasonic transducer 30. A tapered transition piece 32 which is preferably of a frusto conical configuration connects with the transducer 30 and may be fitted at its lower or smaller end closely within the collar 26. This couples the small end of the transition piece 32 with the waveguide 20. The transducer 30 transmits ultrasonic signals which are applied to the transition piece 32 and from the transition piece to the end 24 of waveguide 20. The signals are transmitted along the length of the waveguide to its opposite end 22 and then to the area of the weld 18. Ultrasonic echoes are reflected from the area of the weld back to the end 22 and along the length of the waveguide 20 to end 24. The reflected signals are transmitted through the transition piece 32 to the transducer 30.

In this manner, the transducer system and waveguide act to provide an ultrasonic image of the weld 18 to permit detection of any problems in the weld that could lead to leakage of fluid or otherwise adversely affect the process. As described, the transducer 30 acts as both a transmitter of ultrasonic signals and as a receiver of the reflected signals. An alternative arrangement would be to provide one transducer acting as a transmitter and a second transducer acting as a receiver, with the transmitted signals traveling along one path defined by the waveguide 20 and the reflected signals traveling along a different path provided by the waveguide. In addition, the transducer equipment can be permanently attached to the waveguide end 24 rather than being detachable in the manner previously described.

The flexibility of the waveguide 20 is important, as it allows the waveguide to be bent, curved or formed in virtually any other desired configuration. The surface 14 immediately above the weld 18 may be inaccessible in some applications, and the ability of the waveguide to be shaped as desired thus becomes essential.

As shown in FIG. 2, the transition piece 32 may be a solid element constructed of a material that is suitable for the transmission of ultrasonic signals. Alternatively, as shown in FIG. 3, the transition piece 32 may be a hollow element having its interior filled with a liquid 34 that is suitable for the transmission of ultrasonic signals. In either case, the transition element 32 provides a tapered transition between the transducer 30 and the smaller waveguide 24 which, in the case of FIGS. 2 and 3, is formed by a single fiber. The fiber may be constructed of quartz or some other material that has suitable acoustic properties for transmitting ultrasonic signals.

FIG. 4 depicts an ultrasonic system for inspecting one or more welds 36 which are used to connect a fitting 38 in extension through one wall of a liquid storage tank 40. The tank 40 contains liquid 42 which may be a petroleum based liquid, a chemical that is potentially dangerous, or some other type of liquid. The fitting 38 is submerged well below the surface 44 of the liquid 42 where access to it is restricted. The welds 36 are critical to the liquid storage facility, and leakage or other problems that develop at the welds can lead to serious adverse consequences.

In accordance with the present invention, a flexible waveguide 46 can be manipulated such that its free end 48 is positioned adjacent to the weld 36 that is to undergo inspection. The waveguide 46 may be flexed in a serpentine shape or any other desired configuration, and its opposite end 50 connects with a transition piece 52 which may be of the type shown in either FIG. 2 or FIG. 3, or some other type if desired. The opposite or large end of the transition piece 52 connects with a conventional ultrasonic transducer 54 which operates to apply ultrasonic signals to the transition piece 52 and to receive reflected signals which are returned to the transition piece by the waveguide 46. Manipulation of the waveguide 46 as desired is carried out by a conventional manipulating device 56 which functions in a manner known to those skilled in the field of manipulation of long flexible objects such as the waveguide 46. Again, the flexibility of the waveguide is important because it allows positioning of the waveguide as necessary to reach the critical area.

The equipment may also include a conventional video monitor 58. The waveguide end 50 and the components connected with it are situated at a fixed location above the liquid level in the tank and preferably close to the tank.

In operation, the transducer 54 transmits ultrasonic signals which are applied to the transition piece 52 and then to the waveguide which directs the signals toward the weld 36. The reflected echo signals are received by the tip 48 of the waveguide and transmitted back along the waveguide to the transition piece 52 and the transducer 54 in order to provide an ultrasonic image of the weld area. The ultrasonic image can be examined to detect any flaws or other problems in the weld 36 or at any other critical area that is inaccessible for inspection by conventional techniques.

FIG. 5 depicts a dual element system in which a pair of ultrasonic transducers 60 and 62 are used. The transducer 60 is provided with a pair of side by side fibers 64 and 66. Fiber 64 is used for the transmission of ultra sonic signals toward the area that is to be inspected, as indicated by the directional arrow 64*a*. The other fiber 66 is used for the transmission of reflected echo pulses as indicated by the directional arrow 66*a*. The tips of the fibers 64 and 66 are turned to the side such that the ultrasonic signals that are transmitted and received by them have a horizontal orientation, as the arrows 64*a* and 66*a* illustrate. This shows one version of a possible multiple element system.

The other transducer 62 has a pair of side by side fibers 68 and 70. Fiber 68 is used for the transmission of ultrasonic signals toward the area that is to be inspected, as indicated by the directional arrow 68*a*. The other fiber 70 is used for the receipt of reflected ultrasonic signals, as indicated by the directional arrow 70*a*. The tips of the fibers 68 and 70 are directed downwardly so that the ultrasonic signals they transmit and receive have a vertical orientation, as the arrows 68*a* and 70*a* illustrate.

By using the dual element transducer shown in FIG. 5, inspections can be carried out at the same time in different directions. In many applications, this can facilitate and expedite the inspection procedure and provide ultrasonic imaging information that is complete as to the entire area that is undergoing inspection. Additional fibers can be provided and directed at different orientations if desired.

The waveguides 20 (FIG. 1) and 46 (FIG. 4) can include a single fiber or virtually any number of fibers which are arranged in a fiber bundle which may be of the type shown in FIG. 6. The individual fibers 72 are packed closely together in the bundle which is depicted in FIG. 6. In a waveguide which includes a bundle of fibers, the individual fibers are connected together in the same configuration at both ends of the waveguide but may be disconnected between the opposite ends of the waveguide. This provides the necessary flexibility of the waveguide while assuring accuracy because the locations of the ends of the different fibers are known.

An alternative arrangement of a multiple fiber bundle which comprises the waveguide is shown in FIG. 7. Here, the individual fibers 72 are arranged in ordered rows of fibers which may or may not be packed so closely as to touch one another. FIG. 7 depicts the individual fibers spaced apart from each other.

In the type of bundle shown in FIG. 6 or the type shown in FIG. 7, the individual fiber 72 may serve different functions. For example, some of the fibers 72 are used for the transmission of ultrasonic signals from the transducer and others may be used for the transmission of reflected signals back toward the transducer (or some of the fibers may perform both functions). Other fibers may be used for illuminating the tip end of the waveguide 46. These fibers 72 may be optical fibers of the type that are able to transmit light from a suitable light source such as a laser located in the above ground equipment. Other of the fibers 72 in the bundle may be optical fibers used to transmit optical images from the tip end 48 of the waveguide back to the above ground equipment for display on the video monitor 78. This permits the operator of the equipment to view the area immediately ahead of the waveguide tip 48 in order to enhance his ability to properly manipulate the waveguide so that its tip is positioned properly for inspecting the weld 36. Thus, an actual optical image of the weld 36 may be displayed on the video monitor 58 in order to assist in the proper positioning of the waveguide, and the ultrasonic image of the weld is separately generated for the purpose of inspecting the integrity of the weld or other component that is undergoing examination.

It should be noted that the waveguide may be a probe which moves independently within a larger tube, either axially or rotationally or both. It should also be noted that various types of operations can be carried out along with the inspection. For example, a laser or cutting device can be combined with the waveguide and used to remove unwanted deposits or other material. The ultrasonic imaging equipment provides feedback for use in controlling the removal process.

In addition to the specific applications which are illustrated in the drawings, the flexible waveguide system of the present invention has use in a wide variety of industrial applications. By way of example, laser bored holes are known to be relatively irregular, and the system of this invention can be used to provide an image of the hole geometry and determine the extent of the irregularities. Chemical machining of large surfaces such as panels used in aircraft construction is a commonly used process. A flexible quartz waveguide constructed according to the present invention could be used to make ultrasonic measurements of the part without requiring the part to be removed from the chemical bath as is currently required. The quartz is inert to chemical attack and would greatly improve the process efficiency as well as reducing the errors which can lead to ruined panels. Environments which are otherwise hostile because of chemicals, radiation or other dangerous materials can be made accessible through use of the waveguide.

The monitoring of interior surfaces of vessels or pipe networks is also made possible. Chemical processes can likewise be monitored because the waveguide is able to withstand chemical attack whereas transducers cannot be directly placed at the site of the chemical reactions because caustic chemicals would quickly destroy them. Measurement of pitting caused by corrosion or other deterioration of airframe structures or critical areas in chemical plants is also made possible by embedding the waveguide in the structure which is to be monitored. The monitoring of various other inaccessible areas such as surfaces which are subject to degradation or unwanted deposits can also be carried out.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, we claim:

1. An apparatus for use to inspect an area that is relatively inaccessible and contains unwanted deposits, said apparatus comprising:

a flexible waveguide having opposite first and second ends said waveguide comprising a first optical fiber;

a means connected to said waveguide first end for manipulating said waveguide second end to the inaccessible area;

an illumination means for applying light to said waveguide first end for transmission of the light through said first optical fiber to illuminate the inaccessible area beyond said waveguide second end;

a display means coupled to said waveguide first end for producing a visual image from optical signals transmitted along said first optical fiber from the inaccessible area beyond said waveguide second end so that an operator can observe the inaccessible area and manipulate said waveguide second end into close proximity to the inaccessible area for inspection;

an ultrasonic transducer means coupled to said waveguide first end for transmitting ultrasonic signals through said first optical fiber after said waveguide second end has been manipulated into close proximity to the inaccessible area and for receiving reflected ultrasonic signals along said first optical fiber to provide an ultrasonic image; and a cutting device combined with said waveguide for removing the unwanted deposits from the inaccessible area beyond said waveguide second end.

2. An apparatus in accordance with claim 1 wherein said first optical fiber comprises a quartz material.

3. An apparatus in accordance with claim 1 wherein said display means comprises a video monitor.

4. An apparatus in accordance with claim 1 wherein said ultrasonic transducer means comprises at least one ultrasonic transducer.

5. An apparatus in accordance with claim 1 wherein said illumination means comprises a light source.

6. Apparatus in accordance with claim 1 wherein said cutting device comprises a laser, said laser configured for generating laser radiation for removing the unwanted deposits.

7. An apparatus for use to inspect an area that is relatively in accessible and contains unwanted deposits, said apparatus comprising:

a flexible waveguide having opposite first and second ends, said waveguide comprising a first optical fiber configured to transmit illumination, optical signals, and ultrasonic signals;

a manipulating device connected to said waveguide first end for positioning said waveguide second end;

a light source coupled to said waveguide first end for generating the illumination to be transmitted through said first optical fiber to illuminate the area beyond said waveguide second end;

a video monitor coupled to said waveguide first end for producing a visual image from the optical signals transmitted along said first optical fiber from the area beyond said waveguide second end so that an operator can observe the area and manipulate said waveguide second end into close proximity to the inaccessible area for inspection;

at least one ultrasonic transducer coupled to said waveguide first end for transmitting the ultrasonic signals through said first optical fiber once said waveguide second end has been manipulated into close proximity to the inaccessible area and for receiving ultrasonic signals reflected along said first optical fiber to provide an ultrasonic image of the inaccessible area beyond said waveguide second end; and a cutting device combined with said waveguide, said cutting device configured to remove the unwanted deposits from the inaccessible area beyond said waveguide second end.

8. An apparatus for imaging inaccessible areas in industrial environments and for removing unwanted deposits from the inaccessible areas, said apparatus comprising:

a flexible waveguide adapted for inspection of industrial environments, said flexible waveguide having opposite first and second ends, said waveguide comprising a first optical fiber configured to transmit illumination, optical signals, and ultrasonic signals, said waveguide further configured to be manipulated so that said waveguide second end is adjacent an inaccessible area in an industrial environment;

a light source configured to provide illumination for transmission through said first optical fiber to illuminate the inaccessible area;

a video monitor for producing a visual image from optical signals transmitted through said first optical fiber from the inaccessible area;

at least one ultrasonic transducer for transmitting and receiving ultrasonic signals of the inaccessible area through said first optical fiber;

a cutting device combined with said waveguide for removing the unwanted deposits from the inaccessible area beyond said waveguide second end;

a means connected to said waveguide first end for manipulating said waveguide second end; and wherein said first optical fiber is configured to transmit the illumination, optical signals, and ultrasonic signals.

9. An apparatus in accordance with claim 7 wherein said first optical fiber comprises a quartz material.

* * * * *